United States Patent [19]

Zalisz et al.

[11] Patent Number: 4,870,053
[45] Date of Patent: Sep. 26, 1989

[54] NOVEL COMPOSITIONS AND PROCESSES

[75] Inventors: Rene Zalisz, L'Aumone; Marie-France Salles, Paris, both of France

[73] Assignee: Roussel Uclaf, France

[21] Appl. No.: 567,955

[22] Filed: Jan. 4, 1984

Related U.S. Application Data

[60] Continuation-in-part of Ser. No. 543,990, Oct. 20, 1983, Pat. No. 4,596,709, which is a division of Ser. No. 300,910, Sep. 10, 1981, Pat. No. 4,412,946.

[30] Foreign Application Priority Data

Sep. 19, 1980 [FR] France ................................ 80 20188
Jan. 28, 1983 [FR] France ................................ 83 01345

[51] Int. Cl.$^4$ ...................... C12P 21/00; A61K 37/00; A61K 39/00
[52] U.S. Cl. .......................................... 514/8; 514/2; 530/412; 530/414; 530/417; 530/418; 530/422; 530/424; 424/88; 424/92; 435/68
[58] Field of Search ............... 260/112 R; 424/88, 92, 424/177, 180; 536/1, 4, 18; 514/2, 8; 530/412, 414, 417, 418, 422, 424; 435/68

[56] References Cited

U.S. PATENT DOCUMENTS

| | | | |
|---|---|---|---|
| 4,297,272 | 10/1981 | d'Hinterland et al. | 260/112 R |
| 4,402,939 | 9/1983 | Fournier | 424/92 |
| 4,412,946 | 11/1983 | Zalisz et al. | 260/112 R |
| 4,460,575 | 7/1984 | d'Hinterland et al. | 424/92 |

OTHER PUBLICATIONS

Fournet et al. Chem Abst., vol. 94, No. 180658t, "Medicinal Glycoproteins of *Klebsiella pneumoniae* and compositions containing them".

*Primary Examiner*—Robin L. Teskin
*Attorney, Agent, or Firm*—Bierman and Muserlian

[57] ABSTRACT

A novel process for the preparation of water-soluble acyl glycoprotein extracted from Klebsiella Pneumoniae containing 30 to 45% by weight of proteins, 30 to 40% by weight of neutral saccharides, less than 4% of glucuronic acid, 2 to 5% by weight of osamines with a molecular weight of about 350,000 daltons and having a polysaccharide chain of n chains of one molecule of glucose and 4 molecules of galactose attached to an asparagine of a proteidic chain by a core formed of heptose and 2-keto-3-deoxy-octulosonic acid followed by an acyl portion containing β-hydroxymyristic acid and then N-acetyl-glucosamine designated herein as $F_1$ and compositions and a method of inducing antiallergic properties in warm-blooded animals.

6 Claims, No Drawings

NOVEL COMPOSITIONS AND PROCESSES

PRIOR APPLICATION

This application is a continuation-in-part of our co-pending, commonly assigned U.S. Pat. Application Ser. No. 543,990 now U.S. Pat. No. 4596709 filed Oct. 20, 1983 which in turn is a division of our U.S. Pat. Application Ser. No. 300,910 filed Sept. 10, 1981, now U.S. Pat. No. 4,412,946.

STATE OF THE ART

U.S. Pat. No. 3,855,197 describes a number of glycoprotein extracts including in Example 8 a heterogeneous extract of *Klebsiella Pneumoniae* consisting of a plurality of macromolecules consisting principally of oses and proteins. The composition consists of 3% of lipids, 25% of proteins and 70% glucides which are mainly 58% of neutral oses of glucose, galactose and manose, 10% of glucuronic acid and 1% of N-acetyl-glucosamine.

Commonly assigned British Pat. No. 2,060,645 describes water-soluble glycoproteins extracted from *Klebsiella Pneumoniae* containing 10 to 20% proteins, 50 to 70% of neutral oses, 15 to 25% of glucuronic acid and 1 to 2% of osamines and having a molecular weight of 80,000 to 350,000. The said compositions have antibacterial and immunostimulating activity. The preferred fraction is a neutral homogenous glycoprotein obtained by analytical ultra-centrifugation having 11% of proteins, 89% of glucides which are 70% of neutral oses and 18% uronic acid and about 0% of lipids, and a molecular weight of about 100,000 determined by the method of Yphantis [Biochemistry, Vol. 3 (1964), p. 297] modified by Chevenka [Anal. Biochem., Vol. 34 (1970), p.24-29]. This latter product is about 50% of the product of U.S. patent No. 3,855,197.

Parent U.S. Pat. Application Ser. No. 300,910 filed Sept. 10, 1981 now Pat. No. 4,412,946 describes a process for the preparation of a water-soluble, immunostimulating glycoprotein extracted from *Klebsiella Pneumoniae* containing 30 to 45% by weight of proteins, 30 to 40% by weight of neutral saccharides, less than 4% by weight of glucuronic acid, 2 to 5% by weight of osamines and having a molecule weight of about 350,000 daltons with repeating polysaccharide units of the structure.

wherein m is 3, 4 or 5 and n is a number equal to or slightly different from 94 when m is 5 comprising treating a solution of glycoproteins obtained by diafiltration of an extract of a lysate of Kebsiella Pneumoniae culture with a quaternary ammonium compound, isolating a surnageant by removal of the resulting precipitate, treating surnageant corresponding to a saline solution of glycoproteins in the cold with a low molecular weight alkanol, recovering the resulting precipitate, dissolving the precipitate in water and subjecting the resulting solution to dialysis and then lyophilisis, dissolving the product, filtering the solution through a gel, recovering the first eluted fraction and concentrating the eluant, optionally to dryness.

Studies after the filing of the application determined the structure of the glycoproteins as being acylglycoproteins with the polysaccharide chain being linked to an asparagine of the protein chain by a core formed of heptose and 2-keto-3-deoxy-octulosonic acid followed by an acyl group containing β-hydroxymyristic acid and then N-acetyl-glucosamine.

OBJECTS OF THE INVENTION

It is an object of the invention to provide a novel process for the preparation of acylglycoproteins extracted from *Klebsiella Pneumoniae* designated $F_1$.

It is another object of the invention to provide novel antiallergic compositions and to a novel method of inducing antiallergic activity in warm-blooded animals.

These and other objects and advantages of the invention will become obvious from the following detailed description.

THE INVENTION

The novel process of the invention for the preparation of water-soluble acyl-glycoproteins extracted from *Klebsiella Pneumoniae* containing 30 to 45% by weight of proteins, 30 to 40% by weight of neutral saccharides, less than 4% of glucuronic acid, 2 to 5% by weight of osamines with a molecular weight of about 350,000 daltons and having the proteidic chain composed with about 30% of acid amino acids and having a polysaccharide chain of n chains of one molecular of glucose and 4 molecules of galactose attached to an asparagine of a proteidic chain by a core formed of heptose and 2-keto-3-deoxy-octulosonic acid followed by an acyl portion containing β-hydroxy-myristic acid and then N-acetyl-glucosamine designated herein as $F_1$, comprises treating a solution of glycoproteins obtained by diafiltration of an extract of a lysate of *Klebsiella Pneumoniae* culture with a quaternary ammonium halide, removing the precipitate from the surnageant, concentrating the surnageant by use of an apparatus for molecule selection, treating the cold concentrate with a low molecular weight alkanol, recovering the precipitate and optionally washing the same with a low molecular weight alkanol and drying it.

The novel process of the invention makes it possible to take in a few steps in an economical fashion for an industrial process the concentration of surnageant obtained after removal of the precipitate formed by action of a quaternary ammonium salt. The concentration is preferably effected by use of a device for selection of molecules by selective permeability such as ultra filtration. In effect, this device permits the treatment of a smaller volume in the remainder of the process and in an unexpected manner dispenses with the steps of dialysis and gel filtration of the prior art.

The process of the invention is more surprising in that the prior art process can be reduced particularly by omitting two long and expensive steps and reduces the volume of alkanol used.

The concentration may be effected by the usual methods for molecule selection, especially by the use of permeability selective membranes especially ultrafiltration. Perm-selective membranes have a diverse nature and examples of this type of membrane are cellulose acetate such as membranes of HF-U type sold by Dow Chemicals, or Kalle Chemie, SEPA-CA sold by Osmonics or SM sold by Sartorius, Membranes based on complex polyelectrolytes are UM sold by Amicon or IRIS 3042 sold by Rhone-Poulenc and membranes based on poly sulfones are H10P sold by Amicon and Romicon, SEPA PS sold by Osmonics or IRIS 3022 sold by Rhone-Poulenc. Membranes based on polyamides include BM or BHF sold by Berghof, membranes based on aromatic polymers include PM, MX or HF sold by Amicon and Romicon and the membranes may be based on copolymers of vinyl chloride and acrylonitrile, substituted polyolefines or composites based on polysulfones on a polyethylene support of the PT type sold by Millipore. The membranes may be in sheet or tubular form or in the form of hollow fibers or spirals.

After obtaining the desired acylglycoproteins in pure form, it is preferred to use an ultrafiltration having a threshold cut off which is calibrated for a molecular weight between 5,000 to 100,000 daltons. In a preferred mode of the process, the ultrafiltration is effected with hollow fibers, especially those based on a polysulfone with a threshold cutoff fixed at 5,000 daltons which may be membranes of H10P5 fabric type sold by Amicon and Romicon The concentration operation is preferably effected at about room temperatures of 20° to 30° C., for example. The recommended techniques by the constructor of the membranes used are known and it is possible to use only a single membrane or a plurality of different membranes and the concentration may be effected in a single step or a plurality of steps, continuously or discontinuously.

When hollow fibers are used, the concentration is preferably realized in two treatment cycles using the "wash in" technique which consists of compensation for losses in the filtration chamber of smaller molecules and of the solvent by a supply of solvent in the filtration chamber which is water in the process of the invention. The concentration which is desired to be obtained is about 5 times that of the starting solutions.

The resulting solution when cold is then treated at about 4° C. with a low molecular weight alkanol such as methanol, ethanol, n-propanol or isopropanol, especially ethanol. The most interesting results are those obtained with 6 volumes of ethanol per volume of saline solution overnight at a temperature of 4°C.

The precipitate formed may be isolated by one or more methods such as by decantation followed by filtration, filtration alone or centrifugation.

The recovered precipitate is dried, at room pressure for example, but preferably under reduced pressure in the optional presence of a dehydration agent such as potassium hydroxide, phosphoric anhydride but preferably calcium chloride. The drying can be aided by slight heating, preferably below 40°C. If desired, the precipitate may at this moment be homogenized such as by mechanical grinding.

The precipitate may also be dissolved in water and then dried by atomization or lyophilisation. The lyophilisation may be effected by classical methods such as in freezer-sublimator combination of average size such as commerical SMU or SMRG models sold by Usifroid, lyophilizers of large size such as the combination formed by CA1 freezer and a SMIRS sublimator which are both sold by Usifroid. Smaller laboratory size models may also be used and are sold by other companies such as Serail.

The starting materials for the process of the invention may be prepared as described in U.S. patent application Ser. No. 300,910 using bacteria cultures such as *Klebsiella Pneumoniae* CIP 52,145 which is the same as the strain filed at the Pasteur Institute in Paris under No. I-163. The culture is subjected to lysis dried by lyophilization for example, extracted by a solvent to remove lipids, rid of its proteins then ultra filtered and dried by lyophilization for example.

The antiallergic compositions of the invention are comprised of an antiallergically effective amount of an acyl-glycoprotein extracted from *Klebsiella Pneumoniae* having a polysaccharide chain of n chains of one molecule of glucose and 4 molecules of galactose attached to an asparagine of a proteidic chain by a core formed of heptose and 2-keto-3-deoxyoctulosonic acid followed by an acyl portion containing $\beta$-hydroxymyristic acid an then N-acetyl-glucosamine designated herein as $F_1$ and contains less than 4% of glucuronic acid or an anti-allergically effective amount of a water soluble glycoprotein extracted from a *Klebsiella Pneumoniae* culture which is subjected to lysis, dried by lyophilization, extracted by a solvent to remove lipids, rid of its proteins, then ultra filtered and dried and an inert pharmaceutical carrier or excipient. The compositions may be in the form of tablet, dragees, gelules, syrups, aerosols, suppositoreis, injectable solutions or suspensions, creams or pomades made in the usual manner.

Examples of suitable excipients are talc, arabic gum, lactose, starch, magnesium stearate, cacao butter, aqueous or non-aqueous vehicles, fats of animal or vegetable origin, paraffinic derivatives, glycols, diverse wetting agents, dispersants or emulsifiers preservatives, and colouring and flavouring substances.

The compositions due to their antiallergic properties are useful for the treatment of respiratory allergies such as allergic rhinitis or tracheitis, or laryngitis, cutaneous allergies such as eczema or urticaria, ocular allergies or allergic manifestations or diverse origins such as animal stings or alimentary allergies for example.

The novel method of the invention for the treatment of allergies in warm-blooded animals, including humans, comprises administering to warm-blooded animals an antiallergically effective amount of a water-soluble acyl-glycoprotein extracted from *Klebsiella Pneumoniae* containing 30 to 45% by weight of proteins, 30 to 40% by weight of neutral oses, less than 4% of blucuronic acid, 2 to 5% by weight of osamines with a molecular weight of about 350,000 daltons having the proteidic chain composed with about 30 % of acid amino acids and having a polysaccharide chain of n chains of one molecular of glucose and 4 molecules of galactose attached to an aspargine of a proteidic chain by a core formed of heptose and 2-keto-3-deoxy-octulosonic acid followed by an acyl portion containing $\beta$-hydroxymyristic acid and then N-acetyl glucosamine and designated herein as $F_1$, or an anti-allergically effective amount of a water soluble glycoprotein extracted from a *Klebsiella Pneumoniae* culture which is subjected to lysis, dried by lyophilization, extracted by a solvent to remove lipids, rid of its proteins, then ultra filtered and dried. The above products may be administered orally, rectally, parentally or topically. The daily dose will vary depending on the condition treated and the method of administration.

In the following examples there are described several preferred embodiments to illustrate the invention. However, it should be understood that the invention is not intended to be limited to the specific embodiments.

EXAMPLE 1

1 kg of the product of Example 8 in U.S. patent No. 3,929,994 derived from *Klebsiella pneumoniae* No. I 163 of the Collection of the Pasteur Institute in Paris, France in water at a concentration of 10 g/liter was held at 4° C. for 16 hours and 0.8 volumes of a solution of 3% of cetyltrimethylammonium bromide solution was added at the rate of about one liter per minute. THe mixture was stirred moderately for one hour and was centrifugated at 62,000 g continuously with a flow of 5 liters per hour. The surnageant was concentrated by ultra filtration through hollow fibers with a threshold for fixed retention of 5000 (Hollow Fibers H10P5 sold by Amicon and Romicon) in two treatment cycles in a 5 to 1 proportion. 6 volumes of 96% ethanol were added at a rate of 3 liters per minute and the mixture was moderately stirred for 15 minutes and the decanted mixture was vacuum filtered. The precipitative was rinsed and dried up to 40° C. in the presence of a dehydrating agent and was homogenzied by mechanical grinding to obtain 200 g of product possessing the characteristics of the product of French patent No. 2,490,496 and European Pat. No. 0,049,182.

EXAMPLE 2

Tablets were prepared consisting of 1 mg of the product of Exammple 1 and sufficient excipient of lactose, starch, talc and magnesium stearate for a final tablet weight of 100 mg.

EXAMPLE 3

An aerosol was prepared delivering does of 0.5 mg of the product of Example 1, 0.15 mg of emulsifier and 50 mg of propellant.

EXAMPLE 4

A cream was prepared containing 1 mg of the product of Example 1 and 10 g of an excipient consisting of 2-octyl-dodecanol, ketostearyl alcohol, sodium ketostearyl sulfate methyl p-hydroxybenzoate, propyl p-hydroxylbenzoate and purified water.

EXAMPLE 5

20 g of the product of Example 8 of U.S. patent No. 3,929,994 were dissolved in 2 liters of permuted water and then 1.6 liters of a 3% Cetavlon solution was slowly added thereto. The mixture was stirred for one hour and was then centrifuged at 10,000 rpm for 15 minutes to remove the precipitate. 3 liters of 95% ethanol were added to the surnageant over 15 minutes and the mixture was stirred for one hour and centrifuged at 10,000 rpm for 15 minutes. The surnageant was removed and the precipitate was dissolved in one liter of water. The solution was subjected to dialysis for 48 hours in Visking tubes against permuted water at 4° C. and the resulting solution was lyophilized to obtain 6.2 g of water-soluble glycoproteins, 1 g of which was dissolved in 10 ml of 0.1M ammonium carbonate solution. The resulting solution was passed through a column with a diameter of 2.5 cm and containing 1 liter of Ultragel ACA 34 and elution was effected with 0.1M ammonium carbonate solution. The fraction corresponding to a first elution peak detected with U.V. at 280 nm was recovered and lyophilized to obtain 0.51 g of a purified water solution of glycoprotein containing 30 to 45% by weight of protein, 30 to 40% by weight of neutral saccharides, 2 to 5% by weight of osamines and a molecular weight of about 350,000 daltons.

EXAMPLE 6

0.800 liters of a 3% Cetavon solution was added with stirring to a solution of 20 g of the glycoprotein of Example 8 of U.S. patent No. 3,929,994 in one liter of permuted water and the mixture was stirred for one hour and then centrifuged at 10,000 rpm for 15 minutes. The surnageant was admixed with 1.5 liters of 95% ethanol and the mixture was stirred for one hour and was centrifuged at 10,000 rpm for 15 minutes. The precipitate was dissolved in 0,500 liters of water and the solution was subjected to dialysis for 48 hours in Visking tubes against permuted water at 4°C. The resulting solution was lyophilized to obtain 6.5 g of glycoprotein which was passed through Ultragel ACA 34 by the technique of Example 5 to obtain 3.28 g of water-soluble glycoprotein of the invention.

EXAMPLE 7

Tablets were prepared containing 5 mg of the glycoproteins of Example 5 and sufficient excipient of lactose, starch, talc and magnesium stearate for a final tablet weight of 100 mg.

A pomade was prepared from 200 mg of th eglycoproteins of Example 6 and sufficient excipient for a final weight of 100 g.

EXAMPLE 8

Tablets were prepared consisting of 1 mg of the product of example 8 of US Pat. 3,929,994 and sufficient excipient of lactose, talc and magnesium stearate for a final tablet weight of 100 mg. pcl PHARMACOLOGICAL DATA A. Immunostimulating and mitogenic activity 40 µg of the test compound and 40 µg of bovine albumin serum were administered intraplantary to groups of 10 mice and 10 days later, the mice received intraveinously a non-lethal and non-shocking 100 µg of Serum-albumin. The controls received only serum-albumin in the first injections. The immunostimulating activity was measured as the increase to the response of anaphylactic shock to Serum-albumin and the mitogenic activity was measured by the increase in ganglion weight draining at the point of injection.

The immunostimulating activity was determined by checking the number of animals presenting a state of shock (dyspnea with muzzle cyanosis up to paralysis of rear train, convulsions and death) as well as the dead, 2 hours after the intraveinous injection of Serum-albumin. The results are reported in Table I.

| Product of Example | % of Shocked animals | % Dead animals |
|---|---|---|
| 5 | 60 | 40 |
| 6 | 100 | 50 |
| controls | 0 | 0 |

To determine the mitogenic activity, the surviving animals were killed 2 hours after the interveinous injection of Serum-albumin were taken the popliteal ganglions draining the paw where the injection was and the weight was controlled. The mitogenic activity expressed with index corresponding to the ratio of average weight of ganglion of animal treated with the test product and the control animals treated only with Serum-albumin and the results are reported in Table II.

TABLE II

| Product of Example | Index |
|---|---|
| 5 | 9.1 |
| 6 | 7.2 |

The tests show that the products of Examples 5 and 6 have a very good immunostimulating and mitogenic activity.

B. Stimulation of non-specific defenses

This stimulation was studied by the clearance test of carbon on mice inspired by the technique of Halpern which consisted of injecting an animal in the ocular sinus with a suspension of colloidal carbon and determining as a function of time the kinetics of the disappearance of carbon in the blood effected by measuring the optic density. The products were administered intraperitoneally 24 and 48 hours before the test and the results were expressed as percentage of elimination of carbon particles as compared to controls receiving only the colloidal carbon injection which corresponded to 100% of the number of carbon particles. The results are reported in Table III.

TABLE III

| Product of Example | Dose in mg/kg | % activity - minutes after injection | |
|---|---|---|---|
| | | 8 | 30 |
| 5 | 0.25 | 50% | 70% |
| 6 | 0.25 | 50% | 70% |

Examination of the results shows that the two products provoked an intense stimulation of the defenses of the organism.

C. Acute Toxicity

The $DL_{50}$ dose or dose which killed 50% of mice receiving the product intraperitoneally was determined by the Behrens and Karber method and was 30 mg/kg for the glycoproteins of Examples 5 and 6.

D. Tolerance

The subcataneous injection of 0.2 ml of the glycoproteins of Examples 5 and 6 at a dose of 1000 g/kg in mice did not cause any local or general intolerance.

E. Antiallergic Activity

In this test, allergic subjects synthetize antibodies (E or IGE immunoglobulines) against allergens of which they are senstive and the antibodies are capable of fixing against polynuclear (or granulocytes) basophiles of the subjects and entrain a modification of polynuclear membranes which provokes their degranulation.

The test was inspired by Benveniste Chim. Allergy, Vol. II (1981), p. 1 to 11. One prepared by decantation a plasma enriched in polynuclear basophilies of a subject sensitive to a give allergen starting from a part of blood for 9 parts of colorant (May-Grunwald-Giensal). A control suspension and a suspension containing the test product were left in contact with the same allergen and the percent of degranulation was calculated as follows:

$$\% = \frac{\text{No. of basophiles in control suspension} - \text{No. of basophiles in treated suspension}}{\text{No. of basophiles in control suspension}}$$

An antiallergic agent diminishes the percent of degranulation of polynuclear basophiles.

RESULTS

With cat hairs as the allergen, a concentration of 100 μg of the product of Example 1 per ml did not show any degranulation in the treated suspension for a 61% degranulation of the control suspension.

With the entire body of the mosquitoe as the allergen, concentrations of 2 μg of the product of Example 1 or the starting material of Example 1 per ml did not show any degranulation in the treated suspension for a 60% degranulation of the control suspension.

Various modifications of the products and processes of the invention may be made without departing from the spirit or scope thereof and it should be understood that the invention is limited to be limited only as defined in the appended claims.

What we claim is:

1. A method of treating allergies in warm-blooded animals comprising administering to warm-blooded animals an antiallergically effective amount of an agent consisting essentially of water-soluble acylglycoprotein extracted from *Klebsiella Pneumoniae* containing 30 to 45% by weight of proteins, 30 to 40% by weight of neutral saccharides, less than 4% of glucuronic acid, 2 to 5% by weight of osamines with a molecular weight of about 350,000 daltons and having polysaccharide chain of n chains of one molecule of glucose and 4 molecules of galactose attached to an asparagine of a proteidic chain by a core formed of heptose and 2-keto-3-deoxy-octulosinic acid followed by an acyl portion containing β-hydroxymyristic acid and then N-acetylglycosamine.

2. A process for the preparation of a water-soluble acylglycoprotein extracted from *Klebsiella Pneumoniae* containing 30 to 45% by weight of proteins, 30 to 40% by weight of neutral saccharides, less than 4% of glucuronic acid, 2 to 5% by weight of osamines with a molecular weight of about 350,000 daltons comprising treating a solution of glycoproteins obtained by dialfiltration of an extract of a lysate of a culture of *Klebsiella pneumoniae* with a quaternary ammonium halide, removing the precipitate from the surnageant, concentrating the surnageant by molecular selection, by ultra filtration treating the concentrate at about 40C with a low molecular weight alkanol, recovering the precipitate and optionally washing the same with a lower alkanol and drying the said glycoprotein.

3. The process of claim 2 wherein molecular selection is effected with at least one perm-selective membrane.

4. The process of claim 2 wherein the ultra filtration is effected with a threshold cut-off calibrated to a molecular weight of 5000 to 100,000 daltons.

5. The process of claim 2 wherein the ultra filtration is effected with hollow fibers.

6. The process of claim 5 wherein the hollow fibers are based on polysulfones and are calibrated to 5000 daltons.

* * * * *